United States Patent [19]

Cameron et al.

[11] Patent Number: 4,957,488
[45] Date of Patent: Sep. 18, 1990

[54] THROUGH THE NEEDLE CATHETER DEVICE

[75] Inventors: Robert H. Cameron, Tampa; Robert Doman, Lutz, both of Fla.

[73] Assignee: Critikon, Inc., Tampa, Fla.

[21] Appl. No.: 259,649

[22] Filed: Oct. 19, 1988

[51] Int. Cl.⁵ ............................................. A61M 5/00
[52] U.S. Cl. ........................................ 604/161; 604/158
[58] Field of Search ................................ 604/158–164, 604/177, 180, 263; 606/108

[56] References Cited

U.S. PATENT DOCUMENTS

| | | | |
|---|---|---|---|
| 3,262,449 | 7/1966 | Pannier, Jr. et al. | 604/159 |
| 3,297,030 | 1/1967 | Czorny et al. | |
| 3,335,723 | 8/1967 | Waldman, Jr. | |
| 3,438,373 | 4/1969 | Pannier, Jr. | |
| 3,463,152 | 8/1969 | Sorenson | |
| 3,572,334 | 3/1971 | Petterson | |
| 3,585,996 | 6/1971 | Reynolds et al. | |
| 3,598,118 | 8/1971 | Warren | |
| 3,677,243 | 7/1972 | Nerz | 604/161 |
| 3,677,244 | 7/1972 | Hassinger | 604/161 |
| 3,685,513 | 8/1972 | Bellamy, Jr. | |
| 3,921,631 | 11/1975 | Thompson | 604/160 |
| 4,037,600 | 7/1977 | Poncy et al. | 604/160 |
| 4,401,433 | 8/1983 | Luther | |
| 4,449,973 | 5/1984 | Luther | 604/161 |
| 4,529,399 | 7/1985 | Groshong et al. | 604/159 |
| 4,581,019 | 4/1986 | Curelaru et al. | |
| 4,581,025 | 4/1986 | Timmermans | 604/160 |
| 4,610,671 | 9/1986 | Luther | |
| 4,702,735 | 10/1987 | Luther et al. | 604/161 |
| 4,743,265 | 5/1988 | Whitehouse et al. | 604/161 |
| 4,772,266 | 9/1988 | Groshong | 604/160 |

*Primary Examiner*—Stephen C. Pellegrino
*Assistant Examiner*—Ralph Lewis
*Attorney, Agent, or Firm*—Paul A. Coletti; W. Brinton Yorks, Jr.

[57] ABSTRACT

A through the needle catheter device is described in which a catheter is located inside a splittable needle for insertion into the body. Means are provided for preventing rearward motion of the catheter relative to the needle as the needle and catheter are inserted into the body. As the needle is withdrawn from the body, a splitting mechanism splits the needle, releasing the enclosed catheter. Means are provided for preventing forward motion of the needle relative to the catheter as the needle is withdrawn, thereby preventing inadvertent perforation of the catheter during withdrawal. After the needle has been withdrawn and split, the catheter assembly, including a catheter cannula, a section of extension tubing and a luer, fall away from the patient-facing side of the device. In a preferred embodiment a taping wing is provided at the proximal end of the catheter cannula. The device is preferably made of a transparent or translucent material so that blood flow into the catheter assembly can be visualized by the user.

6 Claims, 6 Drawing Sheets

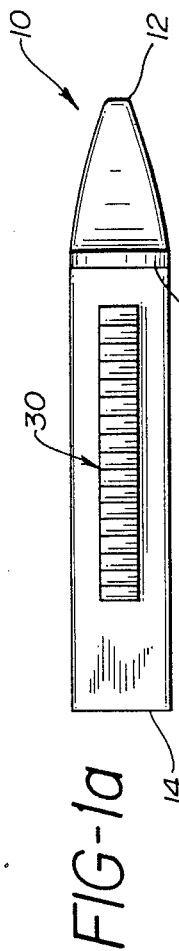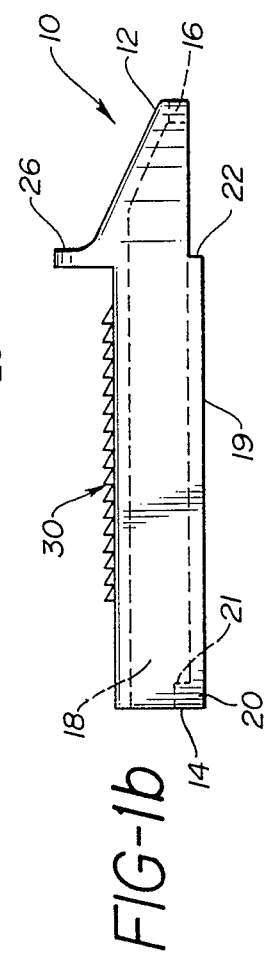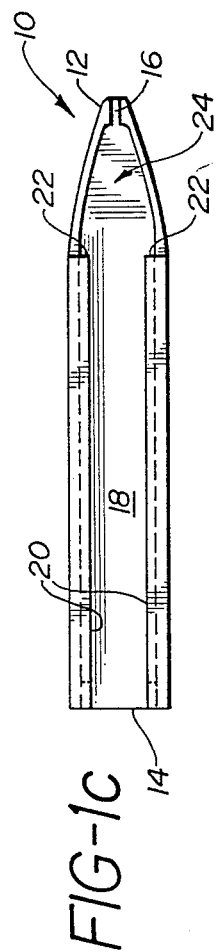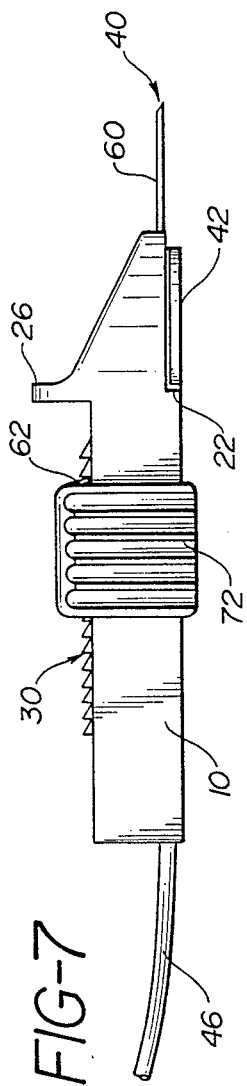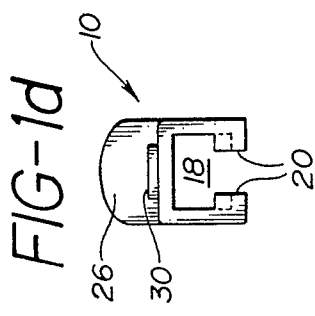

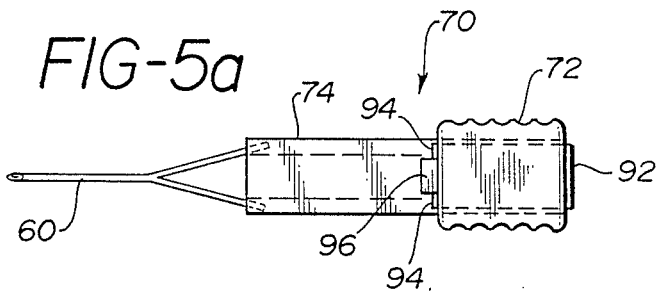
FIG-5a
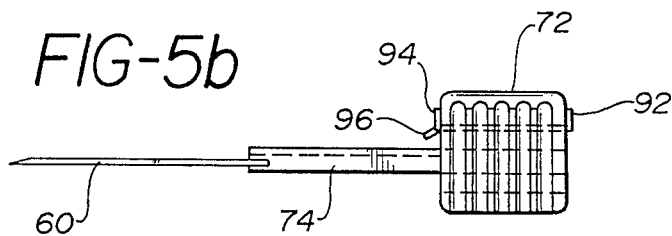
FIG-5b
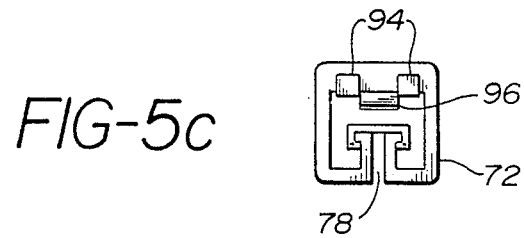
FIG-5c
FIG-5d
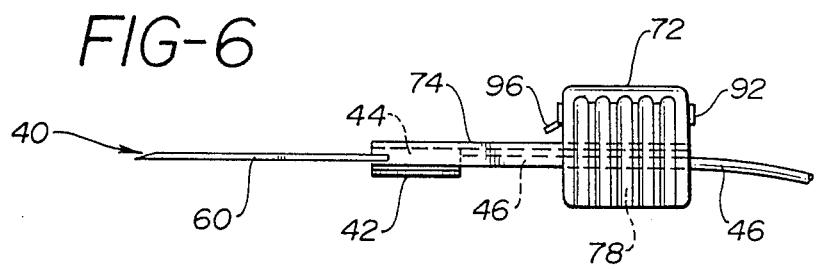
FIG-6

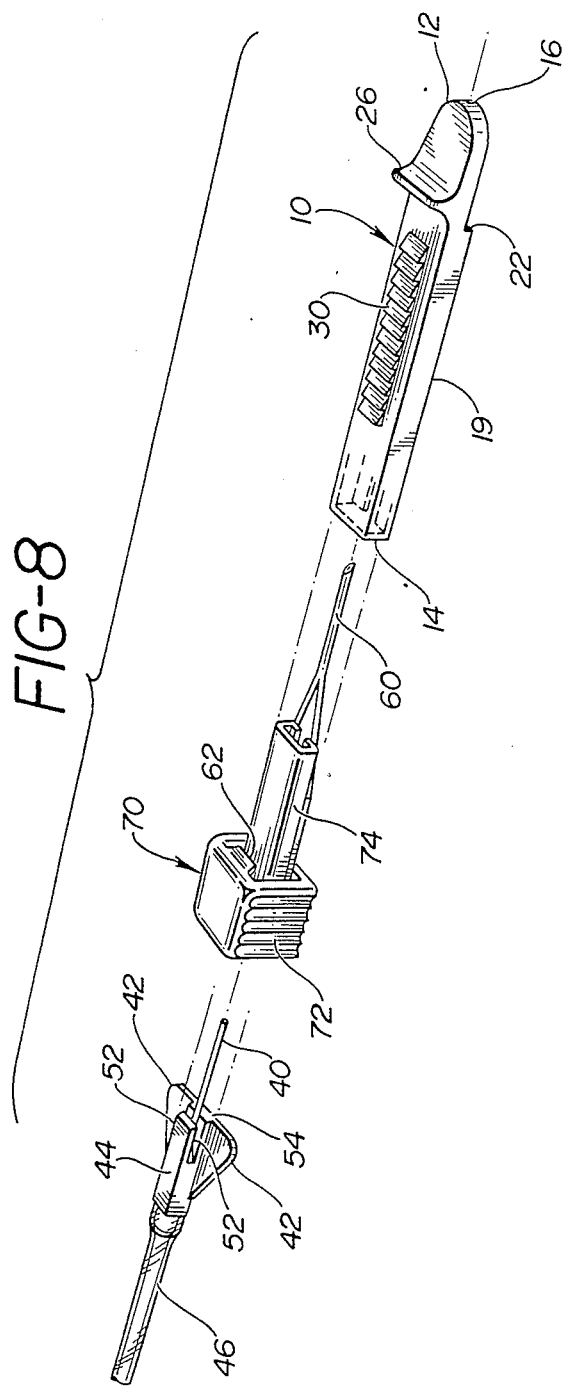

THROUGH THE NEEDLE CATHETER DEVICE

This invention relates to catheter devices for the administration and withdrawal of fluids from a patient and, in particular, to such catheter devices in which a catheter is emplaced by a hollow insertion needle containing the catheter cannula.

Catheters are used in various medical procedures to administer fluids to a patient or to withdraw body fluids from a patient. Since catheters are generally made of a flexible plastic material such as TEFLON or various polymers, a needle is used to access a vein or artery in the body in order to introduce the catheter into a blood vessel. Catheters may be categorized as using one of the two widely known insertion techniques. A first technique is the over-the-needle technique, in which the catheter is initially coaxially mounted on the needle. The needle with its surrounding catheter cannula is inserted through the skin un il the tip of the needle pierces and enters the blood vessel. Proper location of the needle tip is usually noted by a small flow of blood through the needle and into a flash chamber in the needle hub. With the tip of the needle properly located in the blood vessel, the catheter can then slide into the vessel and the needle is withdrawn from the catheter and disposed of. The emPlaced catheter is then usually taped to the skin of the Patient and tubing from a fluid source is connected to an attachment hub on the proximal end of the catheter.

The second insertion technique is known as the through-the-needle technique. In this technique the catheter is initially located inside the lumen of the needle. The needle with its enclosed catheter is inserted through the skin and into the blood vessel until the needle tip is properly located in the vessel. The needle is then withdrawn from the body, leaving the catheter emplaced with the distal end of the catheter cannula located in the vessel. However, the needle cannot be easily removed and disposed of because of the interference of the catheter hub at the proximal end of the catheter. Accordingly, the common solution to this problem with the through-the-needle catheter is to remove the needle from the catheter by splitting it, as is illustrated in U.S. Pat. Nos. 3,596,658; 3,382,872; 4,100,893; 4,306,652; 4,401,433; 4,449,973; 4,559,043; and 4,610,691, among others. As these patents illustrate, the needle may be made splittable by forming the needle of two logitudinally aligned halves, or by longitudinally scoring or perforating the body of the needle. A mechanism is attached to the two longitudinal halves of the needle which may be grasped by the user. As the needle is withdrawn the mechanism is manipulated to split the two halves of the needle apart, thereby separating the disposable needle halves from the enclosed catheter.

The present inventors have found that several problems can arise during the use of a through-the-needle catheter. As the needle and its enclosed catheter penetrate the skin and the blood vessel, the resistance of the tissue being penetrated can oppose the insertion of the catheter. This resistance can cause the distal end of the catheter to retract from the needle tip location. In accordance with a first aspect of the present invention, this problem is overcome by maintaining the longitudinal location of the catheter assembly in a predetermined position relative to the needle assembly during emplacement of the needle and catheter. Inadvertent catheter retraction during insertion is thereby prevented.

Once the needle tip and catheter have been properly located in the blood vessel, the needle can be withdrawn from the insertion site. However, the present inventors have found that it is often desirable to extend or "thread" the catheter into the blood vessel before the needle is withdrawn. When the catheter is threaded into the blood vessel, the user is confident that proper catheter placement has been attained before the needle is withdrawn from the body. In accordance with a second aspect of the present invention, means are provided for advancing the catheter in an extended position from the tip of the needle prior to withdrawal of the needle.

The present inventors have found that a further problem can arise as the catheter is threaded or advanced into the blood vessel and as the needle is withdrawn for splitting. As these procedures take place, the body of the catheter is passing through the distal tip of the needle. Since the needle tip is pointed and sharpened about the lumen, the present inventors have discovered the hazard of accidental perforation or shearing of the catheter by the sharp distal end of the needle. In particular, this hazard is most severe should the needle and catheter reverse their relative direction so that the needle and catheter tips are moving toward one another. In accordance with a third aspect of the present invention, this hazard is reduced by preventing relative movement of the needle tip toward the distal end of the catheter as the needle is withdrawn from the body. In accordance with a further aspect of the present invention, such relative movement is also retarded during advancement of the catheter prior to withdrawing the needle from the body.

A through-the-needle catheter generally comprises two major assemblies: a needle and needle splitter assembly, and a catheter and tubing attachment assembly. In accordance with the principles of the present invention, the catheter and tubing attachment assembly includes a catheter cannula connected to an extension set. The extension set includes a section of microbore tubing connected to the catheter cannula with a Luer connected to the proximal end of the microbore tubing. Proximal the distal end of the microbore tubing is a taping wing, biased in location toward the side of the extension set which is intended to contact the patient when the wing is taped to the patient's body. The taping wing utilizes a flexible, intermediate living hinge, which enables the taping wing to conform to the patient's body. In a preferred embodiment the taping wing is attached to the underside of a catheter hub. When the catheter is threaded into the body up to the catheter hub, which is desired to prevent kinking or "pistoning" of the catheter, the catheter may be affixed in place by taping the wing to the body at the insertion site.

The present inventors have found that numerous ways may be devised to connect the needle assembly to the catheter assembly. However, the present inventors have found that use of a through-the- needle catheter assembly is greatly enhanced by enabling the detachment of the two assemblies by dropping the catheter assembly out from the bottom (patient-contacting side) relative to the needle and splitter assembly. Thus, as the needle is withdrawn from the body and split away from the catheter, the needle assembly can be removed by lifting it upward relative to the body, leaving the catheter assembly in place in its desired position on the body. In the drawings:

FIGS. 1a–1d illustrate various views of a housing for a catheter constructed in accordance with the present invention;

FIGS. 5a–5d illustrate a needle assembly for the catheter of the present invention utilizing the leaf spring of FIG. 4;

FIG. 6 illustrates the needle assembly of FIGURES 5a–5d in engagement with the extension set assembly of FIGS. 2a–2c; and FIG. 7 illustrates a fully assembled catheter constructed in accordance with the principles of the present invention; and FIG. 8 is an exploded view illustrating the assembly of the components of an embodiment of the present invention.

Figure 2A:
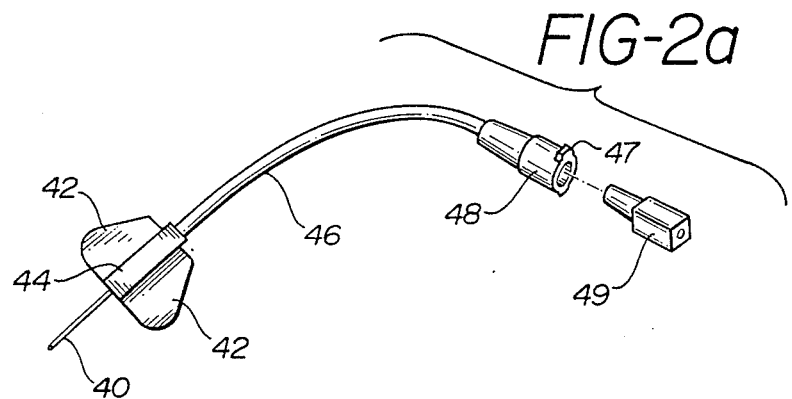
FIGS. 2a–2c illustrate an extension set assembly for the catheter of the present invention.

Referring first to FIGS. 1a–1c, a housing 10 for a through-the-needle catheter of the present invention is shown. The housing 10 is generally elongated in shape and has a distal end 12 through which the catheter and needle extend and a proximal end 14. The needle and catheter extend through an aperture 16 at the distal end when the catheter device is fully assembled. The housing 10 contains a hollow passageway 18 through which the needle assembly may travel. The needle assembly slides on rails 20 which are formed along the bottom 19 of the housing. The rails 20 extend from the proximal end 14 of the housing to their termination at location 22 near the distal end of the housing. The bottom of the housing 10 is open, thereby allowing the extension set assembly to be released through the bottom of the housing. At the proximal end of the rails are end stops 21, which prevent the needle assembly from sliding out the proximal end of the passageway 18. The open bottom of the housing is widened distal the rail termination points 22 to form an open space 24 where the taping wing of the extension set is located in the assembled catheter device.

At the top of the housing 10 is a push tab 26 which is used to insert the needle and catheter. Also formed on the top of the housing are a series of teeth 30. These teeth interact with the leaf of the needle assembly to prevent distal motion of the needle as the needle is withdrawn from the patient.

Figure 2B:
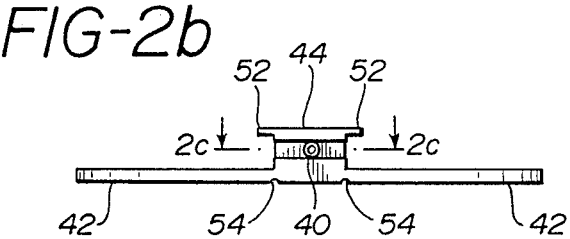
Figure 2C:
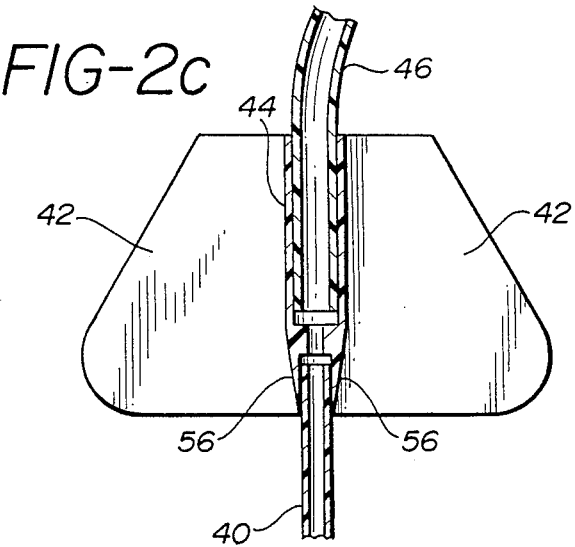

Referring to FIGS. 2a–2c, the extension set assembly of the catheter device of the present invention is shown. At the distal end of the extension set is the catheter cannula 40. The catheter cannula is connected through a junction 44, molded as a part of taping wing 42, to microbore extension tubing 46. As used herein, microbore tubing refers to tubing with an inside diameter of one-eighth inch or less. Microbore tubing is preferred for the extension set because its small interior diameter can be completely filled with only a very small volume of blood. Thus it is possible to detect the passage of blood through the tubing when the needle tip is properly located in the blood vessel after passage of only a small volume of blood into the extension set.

At the proximal end of the tubing 46 is a female luer 48 having luer lugs 47 at the proximal end. A flashplug 49 is inserted into the open end of the luer 48 to prevent the passage of blood out of the luer as the catheter and needle are being inserted. Once the catheter is properly emplaced and the needle is removed, the flashplug is removed and tubing from a fluid source is attached to the luer to supply fluid to the patient.

A view of the distal end of the extension set is shown in FIG. 2b. The taping wings 42 extend outwardly from the junction 44 at the bottom (i.e., patient contacting side) of the extension set. The taping wings are located at the proximal end of the catheter cannula 40, enabling the wings to be taped immediately adjacent the insertion side when the catheter is fully inserted into the body. By taping the wings as close to the insertion site as possible, kinking and pistoning of the catheter cannula is minimized. The taping wings 42 are thinned in the proximity of the junction 44 to form hinges 54 for the wings. The hinged wings can thus bend at the hinges to conform to the shape of the body surface at the insertion site.

The catheter 40 is shown extending from the junction 44. The outer surface 56 of the junction on either side of the catheter and extending proximal the catheter are tapered to form a cam surface. As the needle is withdrawn relative to the catheter by the needle assembly, the needle is split by these cam surfaces 56. It may be appreciated that the cam surfaces could also be formed in the housing 10 at the location of the aperture 16, in which case the surfaces 56 would extend downward from the interior of the housing and be located on either side of the catheter cannula.

The top of the junction 44 is extended to form ridges 52 as shown in FIG. 2b. These ridges enable the junction 44 and the taping wings to be engaged and held in position by the needle assembly prior to needle splitting, as will be discussed below.

FIG. 2c shows the extension tubing 46 and catheter cannula 40 when positioned in the junction 44. The tubing and cannula are affixed in place to form a leak-free fluid path, as by adhesive or ultrasonic bonding. The cam surfaces 56 are also clearly shown in FIG. 2c.

Referring to FIGS. 3a–3d, the needle assembly of a catheter device of the present invention is shown. A splittable needle 60 is attached to the distal end of the needle assembly 70, as by affixing the split ends of the needle into holes in the needle assembly slide 74. Lower edges 76 of the distal slide 74 enable the slide 74 to engage the junction 44 by overlapping ridges 52 of the extension set junction. When so engaged, the extension set is retained in the catheter device prior to the splitting of the needle. The slide 74 extends through the opening 80 of the proximal needle assembly grip 72. The outer dimensions of the slide 74 are determined so that the slide 74 will engage and slide through the passageway 18 of the housing, held in place by the lower rails 20 of the housing. The body of the housing 10 passes through the opening 80 of the grip 72 as the needle assembly slides relative to the housing.

Figure 3A:
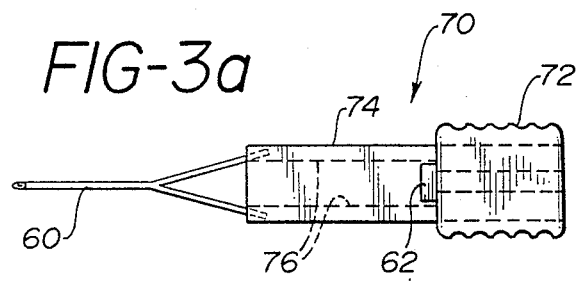
FIGS. 3a–3d illustrate a needle assembly for the catheter of the present invention.
Figure 3B:
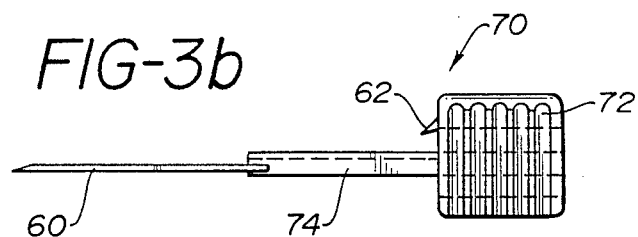
Figure 3C:
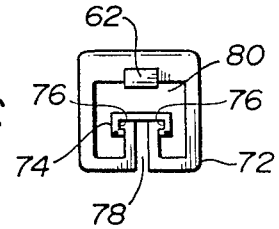
Figure 3D:
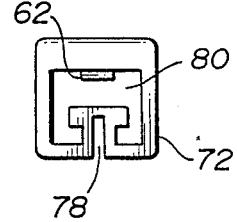

As shown in the top view of FIG. 3a and the side view of FIG. 3b, a leaf or tongue 62 is molded to extend from the distal side of the grip 72. The leaf 62 will engage the teeth 30 on top of the housing as the needle assembly slides in the proximal direction to split the needle. The engagement of the leaf 62 and the teeth 30 prevent inadvertent forward movement of the needle assembly relative to the catheter cannula during needle splitting. The integral leaf 62 is also shown in the front view of the needle assembly of FIG. 3c and in the rear view of FIG. 3d.

The grip 72 has an aperture 78 extending from the bottom of the grip. This aperture is for passage of the extension tubing 46 of the assembled catheter device, and enables the extension set assembly to be disengaged through the bottom of the catheter device.

Figure 4:
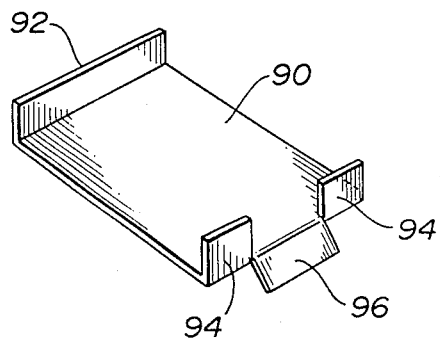
FIG. 4 illustrates a leaf spring for use with the needle assembly of FIGS. 5a–5d.

FIG. 4 illustrates a leaf spring 90 which may be utilized in place of the integral leaf 62. The leaf spring 90 has a proximal upward surface 92, two distal upward surfaces 94, and a tongue 96. FIGS. 5a–5d illustrate the needle assemblY of FIGS. 3a–3d with the leaf spring 90 engaging the grip 72 and functioning in the same manner as the leaf 62.

In FIG. 6, the extension set assembly is attached to the needle assembly 70 by the engagement of the junction 44 within the needle slide 74. The catheter cannula 40 is then located within the splittable needle 60. The extension tubing 46 extends proximal the junction 44 and through the bottom aperture 78 of the grip 72.

FIG. 7 shows the fully assembled through-the-needle catheter device of the present invention, and FIG. 8 is an exploded perspective view illustrating the assembly of the device. As the needle 60 containing the catheter cannula 40 is inserted into the skin, any rearward movement of the catheter is prevented by the abutment of the rear of the taping wings against the lower edge 22 of the housing. When the catheter and needle are properly inserted, as indicated by visible blood in the junction 44 and extension tubing 46, the grip 72 is grasped and the needle assembly is moved to the rear, thereby splitting the needle 60. As the needle assembly 70 moves rearward, the junction 44 disengages from the slide 74 and the extension set is thereafter free to drop from the bottom of the catheter device. The housing and needle assembly are then simply lifted up from the extension set assembly without disturbing the extension set and its emplaced catheter. It may be appreciated that if disengagement of the extension set would have to be done by lifting the extension set upward to remove an underlying housing and needle assembly, the emplaced catheter could readily become dislodged from the blood vessel.

In more conventional over-the-needle catheters, a flash chamber is located proximal the needle to retain and display blood from a proper needle insertion. In the catheter assembly of the present invention such an arrangement is not possible, for the blood initially flows through the catheter, not the needle. Accordingly, in the present invention, the housing, needle assembly and extension set together cooperate to provide the function of the flash chamber. As blood enters the junction 44, it is visible through the junction, which is preferably made of a transparent or translucent material. Likewise, the overlying needle assembly slide 74 and housing 10 are also made of a transparent or translucent material so that the appearance of blood in the junction 44 may be seen through these components. Most preferably all components with the exception of the catheter and needle are translucent or transparent so that blood flow into the junction 44 and extension tubing 46 can be readily seen through the overlying housing and needle assembly.

What is claimed is:

1. A through the needle catheter device in which a catheter is located within a needle having a proximal end and a pointed distal end for accessing a patient comprising:

a needle assembly, including a housing having a patient-facing side and means, connected to the proximal end of said needle, for withdrawing said needle into said housing and splitting said needle; and a catheter assembly including said catheter and suitable for engagement with said needle assembly, and capable of disengaging from said needle assembly from the patient-facing side of said housing.

2. The device of claim 1, wherein at least a portion of said withdrawing and splitting means overlies said catheter assembly, and wherein said needle assembly includes means for viewing blood flow in said catheter assembly through said overlying portion of said withdrawing and splitting means.

3. The device of claim 1 wherein said withdrawing and splitting means is capable of preventing relative motion of the needle and distal end of the catheter toward one another as said needle is withdrawn from said patient.

4. The device of claim 1 further including means, cooperating with said catheter assembly, for preventing proximal motion of said catheter as said catheter and needle are introduced into the body.

5. The device of claim 4 further comprising a taping wing located between said catheter tube and said tubing section.

6. The device of claim 1 wherein said catheter further includes a catheter tube, a luer fitting, and a section of tubing having a first end connected to said catheter tube and a second tube connected to said luer fitting.

* * * * *